(12) United States Patent
Keating

(10) Patent No.: US 6,805,800 B1
(45) Date of Patent: Oct. 19, 2004

(54) METHOD FOR RECOVERING PIGMENTS FROM ALGAL CULTURES

(75) Inventor: Peter James Keating, Serpentine (AU)

(73) Assignee: Beta Carotene Investments Limited, Auckland (NZ)

( * ) Notice: Subject to any disclaimer, the term of this patent is extended or adjusted under 35 U.S.C. 154(b) by 0 days.

(21) Appl. No.: 09/936,213
(22) PCT Filed: Jan. 10, 2000
(86) PCT No.: PCT/NZ00/00001
§ 371 (c)(1), (2), (4) Date: Sep. 10, 2001
(87) PCT Pub. No.: WO01/51162
PCT Pub. Date: Jul. 19, 2001

(51) Int. Cl.[7] ............................. B01D 15/02; B01J 8/20; C07C 403/24
(52) U.S. Cl. ........................ 210/661; 210/691; 585/351; 585/803; 585/820
(58) Field of Search ............................... 210/661, 670, 210/691; 435/67; 568/870; 585/351, 803, 820

(56) References Cited

U.S. PATENT DOCUMENTS 4,284,511 A * 8/1981 Weitzen et al. ............. 210/661
4,554,390 A * 11/1985 Curtain et al. .............. 568/870

FOREIGN PATENT DOCUMENTS

| | | | |
|---|---|---|---|
| DE | 196 38 004 | * | 3/1998 |
| JP | 03-068698 | | 3/1991 |
| WO | WO 92/18237 | * | 10/1992 |

* cited by examiner

Primary Examiner—Ivars C. Cintins
(74) Attorney, Agent, or Firm—Young & Thompson

(57) ABSTRACT

A method and apparatus (101) for the recovery of fat soluble compounds, such as beta carotene, is described. In one embodiment of the invention a solution (102) containing a fat soluble compound is passed through a fluidised bed (104) of crystalline metallic ore particles, such as magnetite, allowing the fat soluble compound to bind to the particles to form a complex (109). The fat soluble compound is released from the complex (109) by passing a wash solution (107) through the fluidised bed and subsequently collected in solution (108). The crystalline metallic ore particles may be reused.

23 Claims, 1 Drawing Sheet

FIG. 1
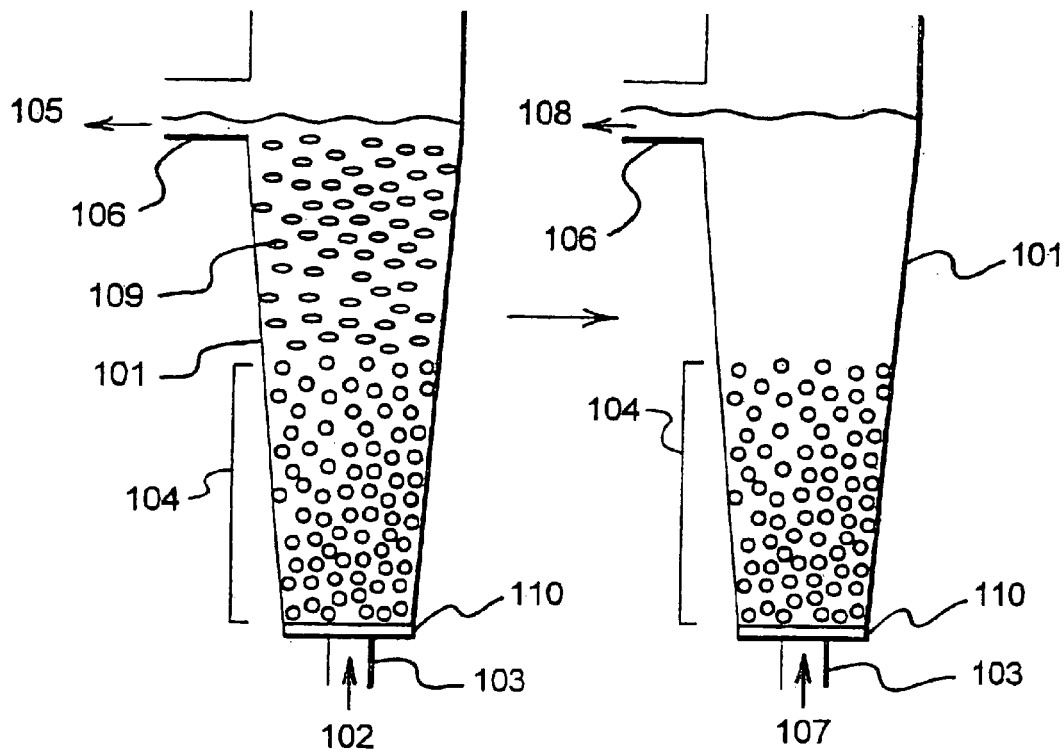
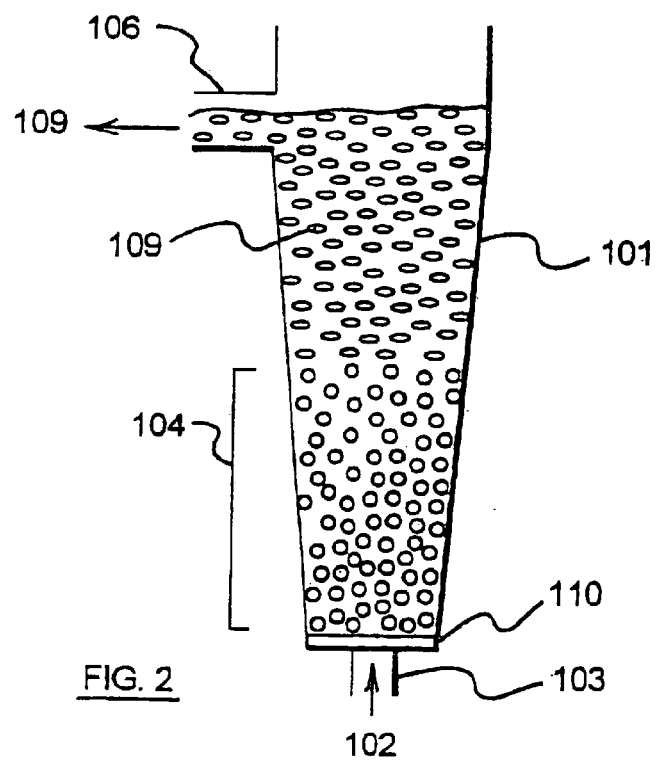
FIG. 2

METHOD FOR RECOVERING PIGMENTS FROM ALGAL CULTURES

FIELD

This invention relates to a method of recovering fat soluble compounds, including but not restricted to pigments such as beta-carotene, from solutions, including but not restricted to those solutions containing microalgal cells.

BACKGROUND

Intensive cultivation of microalgal cells is widely used as the source of a range of biological materials produced by algae including lipids, pigments and protein. A major limitation to the commercial feasibility of manufacturing such materials using algal biotechnology is the fact that microalgal cells exist at relatively low concentrations in water, are of very small size and can be mechanically and osmotically fragile. The harvesting of algal cells and their products at a commercial scale requires processes which concentrate the small algal cells and their constituent chemical products in an efficient manner which is simple, reliable and requires minimal energy inputs.

To date, methods which have been developed involve using either energy requiring processes such as centrifugation and drying, or use low energy processes such as flocculation, settling or algal behavioural responses which are unreliable and inefficient. Other methods require the disintegration of the algal cells which can render any cellular components useless; for example, degradation of valuable components, such as the carotenoids, via oxidation can occur.

One example of a method which may be used to obtain certain cellular components of algal cells, without any adverse degradation of those cellular components, is described in the patent specification relating to PCT/AU82/00165 entitled "Method for Harvesting Algae". This specification concentrates on methods for harvesting and concentrating algae, including Dunaliella, from suspensions of a certain salinity, whereby the whole algal cells are adsorbed onto an appropriate adsorbent media The principle finding relating to this invention is that algal cell membranes become hydrophobic at salt concentrations above 3M enabling them to adsorb onto substances having a hydrophobic surface. A number of suitable hydrophobic adsorbents are described in this specification. In addition, a process of rendering certain adsorbents hydrophobic, or more hydrophobic, by treatment with silanes for example is described.

In PCT/AU82/00165 the whole-cell-adsorbent-media complex is then processed using organic solvents which damage the cell membrane and potentially which allow cellular components, such as beta-carotene, to be released while the cellular debris and insoluble cell components remain adsorbed to the adsorbent media The beta-carotene released into the organic solvent in this invention may contains contaminants such as triterpenoids and other lipids and thus further processing is required to isolate only the beta-carotene.

OBJECT

It is an object of the present invention to provide an improved method of extracting fat-soluble compounds or at least to provide the public with a useful choice.

STATEMENT OF INVENTION

In one aspect of the present invention there is provided a method of extracting fat-soluble compounds from aqueous solutions including the steps:

providing an aqueous solution in which a fat-soluble compound is present;

providing a bed of crystalline metallic ore particles held in an appropriate vessel;

applying the aqueous solution to the bed of crystalline metallic ore particles substantially near the bottom of the bed at a rate sufficient to form and maintain a fluidised bed of crystalline metallic ore particles;

allowing the fat-soluble compound to attach to the crystalline metallic ore particles to form a crystalline-metallic-ore-fat-soluble-compound complex;

providing a wash solution;

contacting the wash solution with the crystalline-metallic-ore-fat-soluble-compound complex to desorb the fat-soluble compound from the complex;

collecting the wash solution containing the fat-soluble compound; and isolating the fat-soluble compound from the wash solution.

Preferably the crystalline metallic ore particles are magnetite particles.

Preferably the wash solution is contacted with the crystalline-metallic-ore-fat-soluble-compound complex by applying the wash solution to the fluidised bed of crystalline metallic ore particles substantially near the bottom of the fluidised bed and at a rate sufficient to maintain the bed in a fluidised state and the resultant wash solution containing the fat-soluble compound is collected from near the top of, or above, the fluidised bed of crystalline metallic ore particles.

Preferably the method further includes the step of collecting the crystalline-metallic-ore-fat-soluble-compound complex prior to providing a wash solution and contacting the wash solution with the crystalline-metallic-ore-fat-soluble-compound complex.

Preferably the crystalline-metallic-ore-fat-soluble-compound complex is collected from a region substantially near the top of the fluidised bed of crystalline metallic ore particles by means of continuous decantation.

Preferably the crystalline-metallic-ore-fat-soluble-compound complex is dried and stored for a period prior to being contacted with the wash solution.

Preferably the fat-soluble compound is present in the aqueous solution within a number of cells and the aqueous solution is a culture media.

Preferably the cells are those of *Dunaliella salina*.

Preferably the fat-soluble compound is a natural pigment.

Preferably the pigment is a carotenoid.

Preferably the carotenoid is beta-carotene.

Preferably the wash solution is an organic solvent.

Preferably the fat-soluble compound is isolated from the wash solution by evaporation or drying.

In another aspect of the present invention there is provided a substantially pure fat-soluble compound obtained using the method of any one of claims 1 to 13.

In yet another aspect of the present invention there is provided a crystalline-metallic-ore-fat-soluble-compound complex obtained using a method as herein described.

FIGURES

These and other aspects of the present invention, which should be considered in all its novel aspects, will become apparent from the following description of the preferred embodiment of the invention, which are given by way of example only, with reference to the accompanying figure in which:

FIG. 1 illustrates a preferred extraction apparatus and method according to the present invention; and FIG. 2 illustrates a preferred extraction apparatus and alternative method according to the present invention.

PREFERRED EMBODIMENT

The preferred embodiment of the invention is described below in terms of the recovery of beta-carotene from water containing the microalgal species *Dunaliella salina* (*D.salina*). It will be appreciated by those of general skill in the art that the invention would be applicable to the recovery of the other carotenoids and to other fat-soluble pigments from *D.salina*, and to the recovery of carotenoids or other fat-soluble compounds or pigments from other suitable organisms. The process of the present invention may also be applicable to the extraction from an aqueous solution of fat-soluble compounds suspended therein.

Throughout the following description the words adsorption and absorption, or derivatives thereof, such as adsorb or absorb, are used. The word adsorb is used to describe how a substance can be held on the surface of another and the word absorb to refer to the inclusion or incorporation of one substance into another. These words have been used interchangeably in the following text as the interactions between the substances (beta-carotene and magnetite) may be referred to in either way. In addition, the word attach is used to cover both adsorption and absorption. Those of general skill in the art will appreciate this factor.

General Principles of the Preferred Embodiment of the Invention

Beta-carotene, is one of a group of compounds called carotenoids; this group also includes alpha carotene, lutene, lutene monoepoxide, astaxanthin, zeaxanthin, canthaxanthin, and lycopene. These compounds are well characterised and those skilled in the art will recognise them as being coloured fat-soluble compounds which finction as part of the light-capturing apparatus in photosynthetic pathways. Beta-carotene, in particular, is a precursor to vitamin A, a vitamin obtained from dietary sources, rather than de novo, in animals. In addition, the carotenoid family have been associated with antioxidant activities. As a result, carotenoids and in particular, beta-carotene, are sought after for use in many food and health products.

The microalgae Dunaliella are typically cultivated in water which has a high concentration of dissolved salts, particularly concentrates of seawater such as those used for the production of salt by solar evaporation. Such waters are very corrosive of metal which they come into contact with. Under conditions of optimal nutrient concentrations, moderate temperatures and intense solar radiation, Dunaliella can grow to concentrations of one million algal cells per ml. The individual cells can contain up to 10% of their weight as beta-carotene, and thus beta-carotene can accumulate to the extent of 15 mg per litre of brine. The rest of Dunaliella cell biomass is composed of protein, carbohydrates and other lipids.

The process of the present invention uses an absortion medium, magnetite, which absorbs betacarotene with very high affinity, but does not absorb significant anounts of the other components of the cell mass. However, beta-carotene is a lipid which is contained within the cell membrane, as opposed to being secreted from the cell and thus free in solution, therefore Dunaliella cell membranes must be disrupted before the beta-carotene is available for absorption.

Magnetite is a crystalline iron ore which has a surface of sharp edges with numerous cracks, crags and irregularities. It has been identified that in the present invention magnetite can be used for the dual purpose of disrupting cell membranes and absorbing beta-carotene. When Dunaliella cells are brought into contact with magnetite particles the cell membrane is punctured by the numerous sharp edges and the cell contents are disgorged into the bulk growth/culture medium.

Another hitherto undescribed property of magnetite is that, because of its unique structure, it selectively absorbs beta-carotene. This occurs as beta-carotene, being a lipid, is insoluble in water and the surface of magnetite crystals are somewhat hydrophobic in nature. When betacarotene is present in an environment of brine and magnetite, it partitions towards the more hydrophobic solid phase than the hydrophilic liquid phase. When the surface of crags within the magnetite particle become coated in beta carotene, a more hydrophobic microenvironment is created in which further beta carotene is absorbed. The total loading of beta-carotene into magnetite is thus very high; for example 2% to 4% of the mass of the magnetite. At this concentration, the void spaces within the magnetite structures are filled with beta-carotene. It will be understood by those of general skill in the art that it will not always be appropriate to load the magnetite completely as it may impact on the downstream recovery of beta-carotene.

Yet another useful property of magnetite disclosed herein is that when beta-carotene is adsorbed onto, then absorbed into magnetite, the oxidation processes which ordinarily cause the rapid decay of beta-carotene, particularly when it is exposed to oxygen, are inhibited such that the magnetite/beta-carotene complex is very stable and does not degrade when exposed to heat or when it is dried.

Because of the above identified properties of magnetite which are not obvious, magnetite. provides an ideal material upon which to collect and concentrate beta-carotene. However, it will be appreciated by those of general skill in the art that alternative absorption media, such as another crystalline metallic ore which has properties equivalent to those of magnetite, for example hematite, may be used in the process of the present invention.

As indicated above when beta carotene has been absorbed on magnetite until the magnetite is saturated, the material is, for example, around 2% by weight beta-carotene. As the brine containing *D. salina* typically has a maximum betasarotene concentration of 20 parts per million, absorption by the magnetite, in this example, thus concentrates the beta-carotene by a factor of one thousand fold. Magnetite typically has a bulk density of 4 Kg per litre whereas the brine used for growing beta-carotene-containing *D.salina* has a bulk density typically of 1.2 Kg per litre. Therefore by passing 1,000 litres of brine containing *D. salina* through one kilogram of magnetite, all the beta-carotene can be removed and contained in a volume of 250 ml, a concentration of almost 4,000 fold.

The beta-carotene can be easily desorbed from the magnetite by simply washing the magnetite with a suitable wash solution such as an organic solvent. Both polar and non-polar solvents are suitable for this purpose. Ordinarily non-polar solvents would not easily mix with a material such as magnetite when it is wetted with water or brine due to hydrophobicity. However, another useful feature of the microcrystalline structure of magnetite is that interfacial tension is broken by the sharp surface, thus a non-polar solvent is easily able to penetrate, and then dewater the magnetite.

The organic solvent used to desorb beta-carotene will contain essentially pure beta carotene, as other microalgal products are not absorbed onto the magnetite. Because the solvent contains pure beta-carotene it is particularly easy to remove the beta carotene and recover the solvent for re-use, for example by using reduced pressure devices such as crystallisers.

Solvents which are suitable for desorbing beta-carotene from magnetite include, but are not restricted to acetone, ethanol, hexane, petroleum ether, or any mixtures of these solvent. Further, due to consumer demand for natural products it is preferable that natural solvents be used. In this regard we have found terpene alcohols to be efficient solvents for use in this invention; for example, cineol (eucalyptus oil), d-limonene (lemon oil), citral (citrus oil) and terpen-4-ol (tee tree oil).

Basic Apparatus and Extraction Example of the Preferred Embodiment of the Invention An example of an apparatus in which the process of the preferred form of the invention may be conducted is shown in Diagram/FIG. 1 and FIG. 2. In FIG. 1 the magnetite is contained within a conical vessel (101). The magnetite sits on a distribution plate, or plenum, (110) which separates the inlet pipe (103) from the vessel interior. This plenum (110) allows a solid phase of magnetite to settle onto the bottom of the vessel when the apparatus is not in use. Brine containing *D. Salina* (102) is introduced at the bottom of the conical vessel via inlet pipe (103) at such a flow rate as to maintain the magnetite as a fluidised bed (104). Being a fluidised bed contactor, there is no prospect for the adsorption media, magnetite, to become clogged. The brine (containing cellular debris) (105) leaves the vessel at outlet pipe (106). It can either be sent into another similar vessel to (101) if it still contains unabsorbed Beta-carotene, or it can be returned to the algal growth pond.

One can see from FIG. 1 that the fluidised bed separates into two different layers or phases. The bottom phase contains primarily magnetite particles and the top phase magnetite-betacarotene complexes (109); which move upwards because of a change in their density due to forming the complex with beta-carotene. It will be appreciated by those of general skill in the art that the layers may not be distinct from one another as illustrated in FIGS. 1 and 2 and that while two layers do form they do so across a gradient as a result of the degree of loading of magnetite with beta-carotene. Further, it will be appreciated that the size of the magnetite particle and the velocity of fluid flowing into the vessel will have an effect on the position of that particle within the vessel. The Figures have been simplified to illustrate that magnetite loaded with beta-carotene will decrease in density during the process.

It should be noted that magnetite of various particle sizes may be used in the present invention. The size of such particles is not important in relation to the absorption of beta-arotene but it will have an effect on the behaviour of the fluidised bed (104). Thus, as a result of the particle size of the magnetite used the flow rate of solutions into the vessel (101) may be required to be altered to maintain the bed (104) in a fluidised state.

The beta-carotene can be desorbed from the magnetite in the top phase by changing the flow into the inlet at (103) from brine to the desorption solvent (107) of choice. A different flow rate is required to keep the magnetised bed fluidised due to the density differences between brine and the solvent. The solvent effluent (108) from (106) contains essentially pure beta-carotene which can be recovered by evaporating the solvent During this stage magnetite present in the top phase may fall to the bottom phase as the beta-carotene is released and its density increases.

It can be clearly seen that by using a number of vessels such as (101), connected in series such that the outlet (106) of one is connected to the inlet (103) of the next vessel in the series, any number of vessels can be connected to each other. If both the inlet and the outlet are connected via a manifold which can feed either brine or desorption solvent into the vessel, then a continuous process cycle of adsorption/desorption/adsorption is possible.

Such a system operates at low pressure, has only valves as moving parts, can be constructed of cheap plastic material and has a very low energy requirement. As such, this system provides a very simple, efficient and reliable means of harvesting beta-carotene from brine.

FIG. 2 uses the same apparatus as FIG. 1 but illustrates an alternative embodiment in which when the magnetite has become progressively loaded with beta-carotene the magnetite-betacarotene complex (109) is collected from the vessel (101) at outlet (106). At this stage the complex can be washed immediately with an appropriate solvent or stored at room temperature for prolonged periods without any significant deterioration of the contained beta-carotene and washed at a later date.

These basic examples will become farther apparent from the specific examples 1 to 3 which follow.

SPECIFIC EXAMPLES RELATING TO THE PREFERRED EMBODIMENT OF THE INVENTION

Example 1

A culture of *Dunaliella salina* was grown in outdoor ponds containing sodium chloride at a concentration of 60 g per litre (approximately 1 M). When the culture had attained a beta-carotene concentration of 9 mg per litre, the culture was pumped into the bottom of a vertical perspex cylinder of 100 mm diameter at a rate of 1.5 litre per minute. When the cylinder became filled with liquid, 800 g of magnetite (120 mesh) was introduced into the top of the cylinder. The magnetic moved towards the bottom of the cylinder but became suspended within the cylinder as a fluidised bed which maintained a height of 400 mm. When the fluidised bed became stable, the culture which passed through the bed to the top of the cylinder was sampled and the beta carotene concentration was measured and found to be 3.9 mg per litre.

While the culture medium was still being pumped through the bottom of the cylinder, a further 400 g of magnetite was then introduced into the top of the cylinder. The fluidised bed then expanded to a height of 580 mm. The culture emerging from the top of the cylinder was again sampled and this time found to have a beta carotene concentration of 1.9 mg per litre. A further 400 g of magnetite was then added to the cylinder which caused the fluidised bed height to increase to 750 mm. At this bed height the culture emerging from the top of the bed appeared clear. The beta carotene concentration was measured and found to be 0.04 mg per litre.

After approximately 1 hour of operation with a total added volume of magnetite of 1,600 g, and a constant upward culture medium flow rate of 1.5 litres per minute, the fluidised bed volume had expanded to 780 mm, and had separated into two distinct zones. The upper zone had a slightly red colour and was 65 mm high. The lower zone was the same black colour as the originally formed fluidised bed and was 715 mm high. There was a distinct boundary between the two layers.

Magnetite material from the upper layer was collected using a pipette, then washed with fresh water and examined under a microscope. There was no sign of any algal cells adhering to this magnetite. The magnetite was then dried in a flow of warm air, weighed accurately and the washed with acetone. The acetone was collected and the beta carotene concentration in the acetone was determined by measuring the optical density at 450 nm wavelength. It was determined in this way that the magnetite contained 3.9% by weight beta carotene.

Example 2

A culture of *Dunaliella salina* was grown in outdoor ponds containing sodium chloride at a concentration of 60 g per litre (approximately 1 M) and magnesium chloride at 60 g per litre (approximately 0.6 M). When the culture had attained a beta carotene concentration of 11 mg per litre, the culture was pumped into the bottom of a vertical perspex cylinder of 100 mm diameter at a rate of 1.4 litre per minute. When the cylinder became filled with liquid, 1,600 g of magnetite (120 mesh) was introduced into the top of the cylinder. The magnetite moved towards the bottom of the cylinder but became suspended within the cylinder as the fluidised bed which maintained a height of 800 mm. When the fluidised bed became stable, the culture which passed through the bed to the top of the cylinder was sampled and the beta carotene concentration was measured and found to be 0.07 mg per litre. The culture medium emerging from the top of the column was examined under a microscope. There were no intact algal cells observed, however cellular debris, comprising mostly broken cell membranes, and halobacteria were observed.

After approximately 2 hour of operation at a constant upward culture medium flow rate of 1.4 litres per minute, the fluidised bed volume had expanded to 845 mm, and had separated into two distinct zones. The upper zone had a slightly red colour and was 165 mm high. At this height the magnetic fluidised bed had reached the top of the perspex cylinder. As the bed expanded further, the top layer spilled over and was collected and was examined under a microscope. There was no sign of any algal cells adhering to this magnetite. The magnetite was then dried in a flow of warm air, weighed accurately and then washed with acetone. The acetone was collected and the beta carotene concentration in the acetone was determined by measuring the optical density at 450 nm wavelength. In this way it was determined that the magnetite contained 3.8% by weight beta carotene.

Example 3

A culture of *Dunaliella salina* was grown in outdoor ponds containing sodium chloride at a concentration of 90 g per litre (approximately 1.5 M) and magnesium chloride at 90 g per litre (approximately 1.0 M). When the culture had attained a beta carotene concentration of 14 mg per litre, the culture was pumped into the bottom of a vertical perspex cylinder of 100 mm diameter at a rate of 1.65 litre per minute. When the cylinder became filled with liquid, 1,600 g of magnetite (120 mesh) was introduced into the top of the cylinder. The magnetite moved towards the bottom of the cylinder but became suspended within the cylinder as a fluidised bed which maintained a height of 800 mm. When the fluidised bed became stable, the culture which passed through the bed to the top of the cylinder was sampled and the beta carotene concentration was measured and found to be 0.06 mg per litre.

In this example the cylinder was modified by creating a spillway 950 mm up the length of the cylinder. After 95 minutes of operation, the upper (red) zone of the fluidised magnetite bed had reached the spillway, and magnetite began trickling from the spillway. This spilled magnetite was separated from the culture medium by decantation. The rate of flow of magnetite trickling from the cylinder was estimated by collecting the material for one minute, removing the culture medium by decantation and weighing the magnetite. It was found that approximately 600 mg of magnetite was spilling from the cylinder each minute. By washing the magnetite with acetone and measuring the optical density of the washing acetone at 450 nm, the spilled magnetite was found to contain 3.65% by weight beta carotene.

For the next 4 hours a 6 g sample of fresh magnetite was added to the top of the cylinder every 10 minutes. The fresh magnetite could be seen to travel through the upper red zone into the lower black zone of the fluidised bed. For the 4 hours during which the trial was undertaken, the fluidised bed maintained a more-or-less constant height and a quite constant rate of red magnetite spillage from the spillway. At the completion of the trial, 400 litres of culture medium had been passed through the cylinder and substantially all the beta-carotene had been removed.

The fluid flow into the cylinder was then switched from culture medium at 1.65 litres per minute to cineole at a flow rate of 2.25 litres per minute. Again a fluidised bed was formed, this time with a bed height of 820 mm. The cineole emerging from the top of the cylinder was a deep red colour. Spectrophotometric measurement of the cineole at 450 nm showed it contained beta carotene at a concentration of 1.35% w/v. After about four minutes of flow, the cineole emerging from the top of the cylinder became a paler red, and after 6 minutes it was clear. All the eluted cineole was collected, and evaporated using a rotary evaporator. As the cineol evaporated, dark crystals of beta carotene were formed. When the cineole had completely evaporated, the remaining crystalline material was collected and weighed. The material weighed 5.44 g.

It can be concluded that the 400 litres of culture originally applied to the magnetite fluidised bed contained 5.6 g of beta carotene. Of this, 5.44 g was recovered in crystalline form from the cineole eluent. This represents a recovery of over 97% of the original beta carotene present in the culture.

Industrial Application and Advantages

Carotenoids and other fat-soluble pigments are sought after additives for food and health products. The process of the present invention is very simple, requires little more energy than that needed to reticulate water containing microalgae to the apparatus and thus provides an efficient means of extracting these compounds from their source and thus may prove of commercial and economic advantage.

The process has the further advantage of stabilising the product and enabling the convenient storage of the product as a concentrate.

What is claimed is:

1. A method of extracting fat-soluble compounds from aqueous solutions comprising the steps of:
   providing an aqueous solution in which a fat-soluble compound is present;
   providing a bed of crystalline metallic ore particles held in a vessel;
   applying the aqueous solution to the bed of crystalline metallic ore particles substantially near the bottom of the bed at a rate sufficient to form and maintain a fluidized bed of crystalline metallic ore particles, wherein the fat-soluble compound is absorbed or adsorbed by the crystalline metallic ore particles to form crystalline-metallic-ore-fat-soluble-compound complex particles, wherein the bulk density of the particulate crystalline-metallic-ore-fat-soluble-compound complex is less than that of the particulate metallic ore, and wherein the fluidized bed forms an upper and a lower zone, the lower zone substantially comprising crystalline metallic ore particles and the upper zone substantially comprising crystalline-metallic-ore-fat-soluble-compound complex particles;

collecting the crystalline-metallic-ore-fat-soluble-compound complex particles from the upper zone of the fluidized bed;

providing a wash solution;

contacting the wash solution with the crystalline-metallic-ore-fat-soluble-compound complex particles to desorb the fat-soluble compound;

collecting the wash solution containing the fat-soluble compound; and isolating the fat-soluble compound from the wash solution.

2. The method as claimed in claim 1, wherein the crystalline metallic ore particles are magnetite particles.

3. The method as claimed in claim 1, wherein the crystalline-metallic-ore-fat-soluble-compound complex is collected by means of continuous decantation.

4. The method as claimed in claim 1, wherein the crystalline-metallic-ore-fat-soluble-compound complex particles are dried and stored for a period prior to being contacted with the wash solution.

5. A method as claimed in claim 1, wherein the fat-soluble compound is present in the aqueous solution with a number of cells and the aqueous solution is a culture media.

6. A method as claimed in claim 5, wherein the cells are those of *Dunaliella salina* (*D. salina*).

7. A method as claimed in claim 5, wherein the culture media is brine.

8. A method as claimed in claim 1, wherein the fat-soluble compound is a natural pigment.

9. A method as claimed in claim 8, wherein the pigment is a carotenoid.

10. A method as claimed in claim 9, wherein the carotenoid is beta-carotene.

11. A method of extracting fat-soluble compounds selected from the group consisting of beta carotene, alpha carotene, lutene, lutene monoepoxide, astaxanthin, zeaxanthin, canthaxanthin and lycopene from aqueous solutions containing *D. salina* cells comprising the steps of:

providing an aqueous solution containing *D. salina* cells in which said fat-soluble compound is present;

providing a bed of crystalline metallic ore particles held in a vessel;

applying the aqueous solution containing the *D. salina* cells to the bed of crystalline metallic ore particles substantially near the bottom of the bed at a rate sufficient to form and maintain a fluidized bed of crystalline metallic ore particles so that the *D. salina* cells are ruptured to release said fat-soluble compound, wherein said fat-soluble compound is absorbed or adsorbed by the crystalline metallic ore particles to form crystalline-metallic-ore-fat-soluble compound complex particles, wherein the bulk density of the said complex is less than that of the particulate metallic ore, and wherein the fluidized bed forms an upper and a lower zone, the lower zone substantially comprising crystalline metallic ore particles and the upper zone substantially comprising said complex particles;

collecting said complex particles from the upper zone of the fluidized bed;

providing a wash solution;

contacting the wash solution with said complex particles to desorb the fat-soluble compound;

collecting the wash solution containing the fat-soluble compound; and isolating the fat-soluble compound from the wash solution.

12. The method as claimed in claim 11, wherein the crystalline metallic ore particles are magnetite particles.

13. The method as claimed in claim 11, wherein the complex is collected by means of continuous decantation.

14. The method as claimed in claim 11, wherein the complex particles are dried and stored for a period prior to being contacted with the wash solution.

15. A method as claimed in claim 11, wherein the aqueous solution is a culture media.

16. A method as claimed in claim 11, wherein the aqueous solution is brine.

17. A method as claimed in claim 11, wherein the fat-soluble compound is beta carotene.

18. A method of extracting beta carotene from aqueous solutions containing *D. salina* cells comprising the steps of:

providing an aqueous solution containing *D. salina* cells in which the beta carotene is present;

providing a bed of crystalline metallic ore particles held in a vessel;

applying the aqueous solution containing the *D. salina* cells to the bed of crystalline metallic ore particles substantially near the bottom of the bed at a rate sufficient to form and maintain a fluidized bed of crystalline metallic ore particles such that the *D. salina* cells are ruptured to release the beta carotene, wherein the beta carotene is absorbed or adsorbed by the crystalline metallic ore particles to form crystalline-metallic-ore-beta carotene complex particles, wherein the bulk density of the particulate crystalline-metallic-ore-beta carotene complex is less than that of the particulate metallic ore, and wherein the fluidized bed forms an upper and a lower zone, the lower zone substantially comprising crystalline metallic ore particles and the upper zone substantially comprising crystalline-metallic-ore-beta carotene complex particles;

collecting the crystalline-metallic-ore-beta carotene complex particles from the upper zone of the fluidized bed;

providing a wash solution;

contacting the wash solution with the crystalline-metallic-ore-beta carotene complex particles to desorb the beta carotene;

collecting the wash solution containing the beta carotene; and isolating the beta carotene from the wash solution.

19. The method as claimed in claim 18, wherein the crystalline metallic ore particles are magnetite particles.

20. The method as claimed in claim 18, wherein the complex is collected by means of continuous decantation.

21. The method as claimed in claim 18, wherein the complex particles are dried and stored for a period prior to being contacted with the wash solution.

22. A method as claimed in claim 18, wherein the aqueous solution is a culture media.

23. A method as claimed in claim 18, wherein the aqueous solution is brine.

* * * * *